United States Patent [19]
Barnicki et al.

[11] Patent Number: 6,018,061
[45] Date of Patent: Jan. 25, 2000

[54] PROCESS FOR RECOVERING 3,4-EPOXY-1-BUTENE

[75] Inventors: Scott Donald Barnicki, Kingsport; Robert Sterling Kline, Jefferson City, both of Tenn.; James Alan Kenning; Anthony Dominick Messina, both of Longview, Tex.

[73] Assignee: Eastman Chemical Company, Kingsport, Tenn.

[21] Appl. No.: 09/305,679

[22] Filed: May 5, 1999

[51] Int. Cl.$^7$ .................................................. C07D 301/32
[52] U.S. Cl. ............................................................. 549/538
[58] Field of Search ............................................. 549/538

[56] References Cited

U.S. PATENT DOCUMENTS

| | | | |
|---|---|---|---|
| 4,897,498 | 1/1990 | Monnier et al. | 549/534 |
| 4,950,773 | 8/1990 | Monnier et al. | 549/534 |
| 5,117,012 | 5/1992 | Stavinoha, Jr. et al. | 549/538 |
| 5,312,931 | 5/1994 | Stavinoha, Jr. | 5549/538 |
| 5,362,890 | 11/1994 | Stavinoha, Jr. et al. | 549/536 |
| 5,618,954 | 4/1997 | Boeck et al. | 549/534 |

OTHER PUBLICATIONS

Kirk–Othmer, "Ethylene Oxide," *Encyclopedia of Chemical Technology*, ed. Mary Howe–Grant, 4$^{th}$ ed., (New York, John Wiley & Sons, 1994), vol. 9, pp 930–933.

*Primary Examiner*—Ba K. Trinh
*Attorney, Agent, or Firm*—Harry J. Gwinnell; Matthew W. Smith

[57] ABSTRACT

A process for recovering 3,4-epoxy-1-butene from a vapor phase catalytic oxidation reactor effluent where 1,3-butadiene is reacted with oxygen over a silver catalyst, the process includes the steps of contacting the reactor effluent with an absorbent in an absorber and vaporizing in the absorber an effective amount of a non-reactive coolant to cool the absorber to a temperature of less than about 40° C. and a pressure of less than about 4 bar. Advantageously, the vaporization of the non-reactive coolant proximate to the absorber allows the absorber to be operated at lower temperatures and pressures than heretofore possible and provides a further advantage of allowing higher $O_2$ concentrations in the feed to the epoxidation reactor.

42 Claims, 5 Drawing Sheets

6,018,061

PROCESS FOR RECOVERING 3,4-EPOXY-1-BUTENE

BACKGROUND OF THE INVENTION

1. Field of the Invention

The present invention relates to a process for recovering 3,4-epoxy-1-butene (EpB) and particularly, to a process for recovering EpB from a vapor phase catalytic oxidation reactor effluent where 1,3-butadiene is reacted with oxygen over a silver catalyst. More specifically, the present invention pertains to a method for the recovery of EpB wherein the EpB laden reactor effluent gas is contacted with a counter-currently moving absorbent stream at temperature of from about 0° C. to about 40° C. and pressures less than about 4 bar absolute.

2. Description of the Prior Art 3,4-Epoxy-1-butene also known as butadiene monoxide and vinyl-oxirane, is an important compound and generally has uses as an intermediate for preparing materials such as tetrahydrofuran and 1,2-butylene oxide. Methods for preparing EpB are disclosed in U.S. Pat. Nos. 5,618,954, 5,362,890 and 4,897,498, the disclosures of which are incorporated herein by reference. One method for the manufacture of EpB so described generally includes the selective epoxidation of 1,3-butadiene (referred to herein as butadiene). The butadiene is contacted with an oxygen-containing gas in the presence of certain silver catalysts.

The rate of epoxidation in the reactor for a given total pressure is related to the mole fraction of oxygen in the epoxidation reactor feed gas. U.S. Pat. No. 5,362,890 discloses that high oxygen concentrations enhance the reaction of 1,3-butadiene to 3,4-epoxy-1-butene. Therefore, it is highly advantageous in the production of 3,4-epoxy-1-butene from 1,3-butadiene to operate the epoxidation reactor with a feed gas containing as high an oxygen content as possible, concomitant with safe operation outside of the explosive limits.

As explained in Lees, F. P., "Loss Prevention in the Process Industries, Volume 1," 485–86 (1980), a flammable gas, e.g., methane, butane, and other alkane hydrocarbons, burns in oxidizing environments only over a limited composition range. The limits of flammability (often called the explosive limits) are the concentration extremes of: high oxygen and low combustible mixture, and low oxygen and high combustible mixture at which a mixture of a flammable gas and an oxidant can continue to burn once a flame is ignited by an external energy source such as a spark. These flammability extremes are a function of temperature, pressure, and composition. The explosive limit is usually expressed as volume or mole percent flammable gas in a mixture of oxidant (usually oxygen), inert, and flammable gas. The smaller value is the lower (lean) limit and the larger value is the upper (rich) limit. Typically, the safe operating range for a given flammable gas and oxidant mixture decreases as temperature and pressure increase, and amount of inert decreases. Increases in pressure have a larger effect than the increases in temperature. The explosive limits of flammable gas mixtures, e.g., n-butane and 1,3-butadiene, can be estimated by the well-known LeChatlier's rule.

EpB is a very reactive compound which requires the recovery operations to be performed under mild conditions to avoid the conversion of EpB to other undesired compounds such as butenediols and oligomers. It is possible to recover EpB directly from the epoxidation effluent by compressing the gaseous effluent to pressures sufficiently high to liquefy the EpB. However, the compression of the effluent would require the use of a series of compressors and heat exchangers to remove the heat of compression and maintain the EpB at a temperature which would minimize by-product formation.

The recovery of gaseous products by absorption wherein a gaseous stream is contacted with a liquid absorbent, also referred to as an extractant or solvent, is well known. For example, in ethylene oxide processes wherein ethylene is epoxidized to ethylene oxide, ethylene oxide is recovered from the epoxidation reactor effluent gas by counter-current contact with a solvent having water as the main component. Crude ethylene oxide is recovered from the EO-laden water stream from the bottom of the absorption zone by distillation or depressurization and stripping with steam. The water remaining after stripping of ethylene oxide is recycled to the EO absorption zone for reuse. Such a system is described, for example, by Dever et al in the *Kirk-Othmer Encyclopedia of Technology*, 4$^{th}$ Edition, "Ethylene Oxide", 930–933 (1994).

One problem with the above-described recovery process is a significant amount of the ethylene oxide reacts with the water to produce ethylene glycol. During the recovery of ethylene oxide vapor in the absorption column and during the subsequent stripping or distillation of the recovered ethylene oxide-water mixture, it is impossible to prevent the conversion of a substantial fraction of the ethylene oxide to ethylene glycol via the reaction with water. Such losses to ethylene glycol can reach 3 to 20 percent or higher of the ethylene oxide originally present in the gas phase reaction effluent and represent a large economic penalty for operations where ethylene glycol is not a desired product. However, since EpB has very limited water solubility, water is not a practical absorbent for the recovery of EpB. Accordingly, other methods of separating the EpB from the other epoxidation reactor effluent constituents have been desired.

U.S. Pat. No. 5,117,012 discloses a process for the recovery of EpB by contacting the vaporous oxidation reactor effluent having EpB, butadiene, an inert diluent gas, and oxygen with liquid butadiene in an absorption zone to obtain a solution of EpB in butadiene. The inert diluent gases specifically contemplated by the '012 patent are nitrogen and methane. The '012 patent discloses contacting the reactor effluent with liquid butadiene at a pressure of about 5 to 15 bar and at a temperature of about 0° C. to about 30° C. Such high pressures result in a number of disadvantages, such as, the capital and operating costs for the compressor(s) required to achieve the high pressures, EpB losses through hydrolysis and oligomer formation caused by the temperatures produced by the compression of the reactor gas effluent, and butadiene losses due to polymerization resulting in lower overall yields and downtime.

U.S. Pat. No. 5,312,931 discloses a process for the recovery of 3,4-epoxy-1-butene from a vapor phase epoxidation effluent by counter-current contact with a mixture of liquid butane and butadiene in an absorption zone. The absorber is operated at a pressure of from about 3 bars to about 6 bars and a temperature of about 0° C. to about 40° C. Although the '931 patent teaches an improvement over the '012 patent, the butane/butadiene recovery process also has disadvantages. In order to ensure that the absorbent butane/butadiene largely remains a liquid within the absorption zone at operating temperatures that can be achieved with an inexpensive cooling medium such as water, i.e., above at least about 30° C., the absorption zone must be operated at a pressure of at least about 4.2 bars. Because of the dominance of pressure effects on explosive limits, the maximum safe oxygen content of the epoxidation recycle gas is generally dictated by the highest pressure point in the recycle loop, i.e., by the pressure at the outlet of the recycle compressor. For example, with a typical mixture of butadiene and n-butane diluent in the reactor effluent gas, the maximum safe oxygen content at a compressor outlet pressure of about 5 bar or greater and a reasonable compressor outlet temperature of 85° C., is less than 28 mole percent.

If the absorption zone could be operated at lower pressure and the compressor outlet pressure could be lowered, e.g., to less than 4 bar, then the maximum safe oxygen content would be greater than about 31 mole percent oxygen. For a given oxygen concentration, the process could be operated farther from the dangerous upper explosive limit and would be safer. However, operating at lower pressures, and concomitantly lower temperatures is quite costly if the required low temperature cooling is supplied by ordinary means to those skilled in the art such as chilled brine or glycol refrigeration units. Moreover, high inlet reactor pressure, i.e., above about 3 bar, adversely affects EpB production. The reactor effluent normally exits the reactor at low pressure, e.g., less than 3 bar, normally 1.0 to 2.0 bar. To meet the aforementioned temperature and pressure requirements for absorption with a mixture of butane and butadiene, the reactor effluent is first compressed to a suitable pressure, i.e., greater than about 4.2 bars, prior to its introduction into the absorption zone. The higher pressures and resulting polytropic temperature rise within the compression zone in the presence of high concentrations of 3,4-epoxy-1-butene can cause formation of polymeric materials which deposit on the walls of the compressor and associated piping. The build-up of such polymeric material reduces the operating efficiency of the compressor and can lead to permanent equipment damage and frequent process shutdowns for maintenance, with subsequent loss of production and revenues. Moreover, the compression ratio of the compressor would be reduced, resulting in lower equipment cost.

Accordingly, there is a need for a process for efficiently and economically recovering 3,4-epoxy-1-butene from a vapor phase epoxidation reactor using low temperature and pressure conditions.

SUMMARY OF THE INVENTION

It has been discovered that EpB can be recovered from a substantially vaporous epoxidation effluent having constituents of EpB, butane, butadiene, and oxygen by intimately contacting the vaporous effluent with a liquid absorbent or solvent in an absorption zone, such as an absorber, operating at a temperature of less than about 40° C. and a pressure of less than about 4 bar. As used herein, the terms "absorbent" and "solvent" are used interchangeably for describing a material or composition that will preferentially absorb a targeted compound, such a EpB, from another stream composed of the targeted compound and other constituents. The process for recovering EpB includes the steps of contacting the vaporous epoxidation effluent in an absorbent zone with an effective amount of a liquid absorbent to absorb essentially all of the EpB present in the vaporous reactor effluent and vaporizing in or near the absorber an effective amount of a non-reactive coolant to cool the absorbent zone to a temperature of less than about 40° C. and a pressure of less than about 4 bar. As used herein, "absorbent zone" and "absorber" are used interchangeably as one skilled in the art will recognize that each performs a substantially similar function and accordingly, will be referred to herein as "absorber".

Another aspect of the invention is a process for recovering EpB from a substantially vaporous epoxidation effluent which includes the steps of contacting the epoxidation effluent in an absorber with an effective amount of the liquid absorbent to absorb essentially all of the EpB to produce an EpB lean vaporous effluent and an EpB rich first liquid effluent, condensing at least a portion of the vaporous effluent to form a second liquid effluent, returning at least a portion of the second liquid effluent to the absorber at a pressure greater than the absorber pressure and desirably, returning the condensed second liquid effluent at a pressure greater than about 4 bar, and vaporizing a portion of the returned second liquid effluent in or near the absorber to produce a temperature of less than about 40° C. and a pressure of less than about 4 bar in the absorber.

Another aspect of the invention provides a process for recovering EpB from a substantially vaporous epoxidation effluent which includes the steps of contacting the epoxidation effluent in an absorber with an effective amount of a liquid absorbent to absorb essentially all of the EpB and form a first liquid effluent and a vapor effluent, condensing at least a portion of the vapor effluent to form a second liquid effluent; recovering at least a portion of the absorbent from the first liquid effluent to form a third liquid effluent, and returning at least a portion of the second and third liquid effluents to the absorber at a pressure greater than about 4 bar.

Another aspect of the invention provides a process for recovering EpB from a substantially vaporous epoxidation effluent and includes the steps of contacting the epoxidation effluent in an absorber with an effective amount of a first liquid absorbent to absorb essentially all of the EpB and form a vapor effluent, contacting the vapor effluent with a second liquid absorbent in a second absorber to absorb a substantial portion of first absorbent, separating the first and second absorbents, recycling the second absorbent to said second absorber and the first absorbent to the first absorber at a pressure greater than about 4bar.

It is an object of the present invention to provide a process for the recovery of EpB from a vapor phase epoxidation reactor wherein the absorber is operated at a pressure of less than about 4 bars and a temperature of less than about 40° C.

It is another object of the present invention to provide an integrated absorption-absorptive refrigeration process for the recovery of 3,4-epoxy-1-butene from a butadiene epoxidation reactor wherein the absorber is operated at a pressure of less than about 4 bars and a temperature of less than about 40° C.

It is another object of the present invention to provide a process for substantial recovery of 3,4-epoxy-1-butene from a butadiene epoxidation reactor wherein the absorber is operated at a pressure of less than about 4 bars and a temperature of from about 0° C. to less than about 40° C. in an efficient and economical manner.

These and other objects and advantages of the present invention will become more apparent to those skilled in the art in view of the following description and the accompanying drawings wherein like parts and objects have similar reference numerals. It is to be understood that the inventive concept is not to be considered limited to the constructions disclosed herein but instead by the scope of the appended claims.

DETAILED DESCRIPTION OF THE PREFERRED EMBODIMENTS

Figure 1:
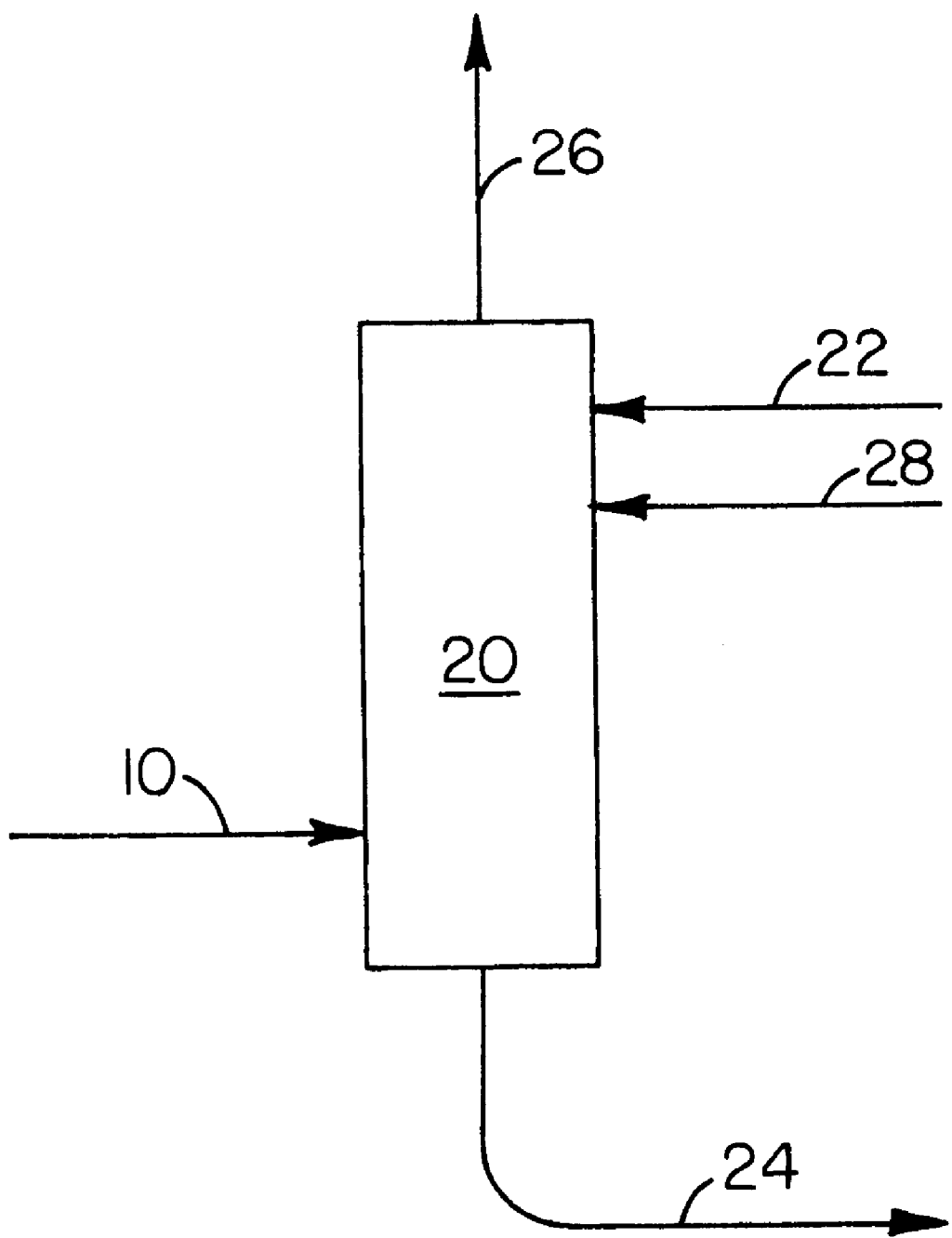
FIG. 1 is a schematic view of one embodiment of the process for recovering vaporous EpB from an epoxidation reactor effluent.

The process of the present invention may be used in combination with any epoxidation process wherein butadiene is contacted with an oxygen-containing gas in the presence of a catalyst to produce an epoxidation effluent comprising EpB, butane, butadiene, and oxygen. The silver-catalyzed, epoxidation processes described in U.S. Pat. Nos. 4,897,498 and 4,950,773 are typical of those which may be employed. The gaseous epoxidation effluent typically contains from about 0.5 to about 10 mole percent EpB and preferably from about 1 mole percent to about 7 mole percent, about 4 to 50 mole percent butadiene, and about 25 to 85 mole percent inert (butane) gas. The effluent also contains a total of about 0.5 to 10 mole percent of other constituents such as, water, carbon dioxide, acrolein, furan, vinylacetaldehyde, and crotonaldehyde, formed in the epoxidation reactor. Unconsumed organic halide also is present in the epoxidation effluent. Heretofore, the epoxidation effluent was typically fed to a cooling/compression zone comprising at least one heat exchanger and at least one compressor to compress the effluent to a pressure of about 3 to about 10 bars absolute and cooled to a temperature of about 0° C. to about 100° C. The cooling and compression of the effluent could include a gas/liquid separator to remove any condensed liquids, such as, water and/or butenediols (3-butene-1,2-diol and 2-butene-1,4-diol), from the pressurized and cooled effluent prior to feeding it to the absorption zone. If the effluent is not cooled and compressed, the temperature and pressure within the epoxidation reactor product line can be from about 1.0 to about 4.0 bar and at a temperature of from about 25° to about 150° C., and more typically from about 1.0 to about 2.0 bar and from about 30° C. to 80° C.

While the present invention is susceptible to alternative embodiments in various forms, there are shown in the drawings of FIGS. 1–5, and hereinafter described in detail, preferred embodiments of the invention. However, the present disclosure is to be considered as an exemplification of the invention without limitation to the specific embodiments illustrated. The pressures referred to herein are given in bars absolute.

FIG. 1 illustrates a schematic flow diagram of one embodiment of the present invention for recovering EpB from the effluent of an epoxidation reactor described above. The reactor effluent includes, as majority constituents, EpB, butane and butadiene. The recovery process includes contacting the epoxidation reactor effluent with an effective amount of a liquid absorbent to absorb essentially all of the EpB present in the epoxidation reactor effluent and vaporizing in or near the absorber, an amount of a non-reactive coolant to cool the absorber to a temperature of less than about 40° C. and a pressure of less than about 4 bar. With specific reference to FIG. 1, the epoxidation effluent is fed via line 10 to the lower section of an absorber 20. An absorbent is fed to the upper section of the absorber 20 via line 22, and desirably near the top, of the absorber 20. The absorbent flows downward, that is, counter-current to the flow of the gaseous effluent entering the absorber 20, absorbing or scrubbing the EpB component from the upwardly-flowing epoxidation effluent. In accordance with the invention, a substantially non-reactive coolant or refrigerant is introduced into the absorber via line 28. The coolant enters the absorber 20 at a pressure substantially greater than the operating pressure of the absorber 20 so that as the coolant enters the absorber 20 it vaporizes, causing cooling by direct contact with the absorber 20, the absorbent, and/or reactor effluent in the absorber 20. Alternatively, the coolant and absorbent can be intermixed and introduced into the absorber 20 in the same line 22, 28 or both, in which case the feed line will contain both absorbent and coolant constituents. Desirably, the absorber 20 and its contents are cooled to a temperature of less than about 40° C. Preferably, the absorber 20 and its contents are cooled to a temperature of from about 0° C. to about 40° C. and are at a pressure of about 1.0 to about 3.5 bar, and more preferably, the absorber 20 and its contents are cooled to a temperature from about 2° C. to about 15° C. and are at a pressure of about 1.0 to about 3 bar and most preferably are at a pressure of from about 1 to about 2 bar.

The absorber 20 typically comprises a columnar, pressure vessel containing trays or a packing material which facilitates intimate gas/liquid contact. The gas/liquid contacting equipment in the absorber 20 may include, but are not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. *Distillation Design*, McGraw-Hill, N.Y. (1992), Chapters 6 and 8 the disclosures of which are incorporated herein by reference. Depending on the choice of absorbent and the absorbent flow rate of stream 22, the absorber 20 contains trays or packing equivalent to 5 to 25 theoretical equilibrium stages, more preferably 8 to 15 theoretical stages. The amount of EpB present in upper gas stream 26 is determined by the absorbent flow rate and the number of stages in absorber 20, but typically is less than 0.1 weight %, preferably less than about 0.05 weight %, and more preferably less than about 250 ppm EpB. The EpB-laden absorbent exits the bottom of the absorber via line 24 and has from about 5 to about 50 weight percent and more preferably from about 10 to about 40 weight percent EpB.

The absorber 20 may also include a means, such as a disengaging space above the packing, to prevent or minimize entrainment of liquids in the gas stream removed from the absorber's upper section.

The absorbent should be substantially non-reactive toward EpB and have good solubility for EpB. Hydrocarbons with normal boiling points within about 30° C. of EpB, such as pentane, hexane, cyclohexane, heptane, and the like form azeotropes with EpB. Although such hydrocarbons may be used they are not preferred since they make separation of EpB from the absorbent 22 quite difficult. The use of aromatic hydrocarbons, such as benzene, toluene, or xylene, and their presence in the EpB production system causes a decrease in the activity of the silver epoxidation catalyst. Suitable absorbents include, but are not limited to, $C_3$ to $C_{20}$ hydrocarbons which do not form azeotropes with EpB, $C_4$ to $C_{20}$ alkanols, $C_6$ to $C_{22}$ carboxylic acid esters, $C_2$ to $C_4$ carbonates and combinations and mixtures thereof. N-butane, isobutane (collectively butane) isopentane and mixtures thereof are preferred because they have no effect on the epoxidation reaction, do not form azeotropes with EpB, and exhibit favorable explosive limit characteristics.

A mixture of butane and 1,3-butadiene may also be use as an absorbent. The butane:butadiene mole ratio of the liquid mixture with which the effluent is contacted is about 20:1 to 1:2 with mole ratios of about 12:1 to 2:1 being preferred. As used herein, the term butane refers to C-4 hydrocarbons in general such as normal butane, isobutane, cyclobutane and mixtures thereof. Desirably, the butane includes approximately 95% n-butane with minor amounts of other C-4 and C-5 compounds. The use of a mixture of butane and butadiene as the absorbent is economically advantageous as compared to the use of other organic materials which are extraneous to the EpB production system. For example, the use of another absorbent would increase costs due to the additional equipment required for its recovery in addition to the added cost of the absorbent material itself. Since butane can function as both the reactor diluent and an absorbent component the number of components in the process are minimized. Additionally, the use of a mixture of butane and butadiene reduces compression and utility costs since a much lower pressure is required for recovery of the EpB.

Coolants or refrigerants suitable for cooling the absorber and the various constituents therein include, but are not limited to, $C_3$ to $C_5$ hydrocarbons, chlorofluorocarbons, hydrofluorocarbons, and perfluorocarbons with normal boiling points between –42° C. and 15° C. Butane is preferred and in a particularly preferred embodiment the coolant and absorbent both include butane. To provide the auto-cooling effect, the coolant entering the absorber has a pressure greater than the pressure of the absorber 20. Desirably, the coolant has a pressure greater than about 4 bar with pressures from about 5 bar to 12 bar being preferred and pressures of about 5 bar to about 7.5 bar being more preferred. Prior to entering the absorber 20, the temperature of the coolant can be from about 0° C. to about 80° C. with temperatures from about 20° C. to about 60° C. being preferred.

The amount of liquid absorbent and coolant fed to the absorber 20 can vary substantially depending on, for example, the particular vessel configuration, the use of packing material and its type, and the feed rate and composition of the epoxidation effluent. Generally, the weight ratio of the absorbent feed via line 22 to epoxidation effluent feed via line 10 is in the range of about 1:10 to about 1:1. The temperature of the liquid absorbent feed is in the range of about 0° C. to 40° C.

In the case where butane and 1,3-butadiene are predominantly used as the absorbent and/or coolant, the butane:butadiene mole percents in the absorber are maintained to provide an absorber gas effluent, via line 26, having from about 4 to about 50, preferably about 7 to about 20, mole percent of butadiene, and about 25 to about 85, preferably about 40 to about 80, mole percent of butane. The ratio of butane to butadine in the absorber also determines the concentration of these components in the vaporous effluent 26 from the absorber 20. As used herein, "predominantly" means that the stream may contain other material(s)s that do not substantially alter or interfere with the mixture of butane and butadiene absorbing EpB. It is to be further understood that such non-interfering material(s) may be present, volumetrically, in substantial or insubstantial quantities relative to that of the amount of butane and butadiene used.

A liquid effluent comprising an EpB rich solution in butane and butadiene is removed from the base of the absorber 20 via line 24 and is fed to an EpB recovery zone, described in greater detail below, where the EpB is substantially separated from the accompanying absorbent and coolant. An example of such butane/butadiene recovery zone is described in U.S. Pat. No. 5,312,931, the disclosure of which is incorporated herein by reference. As is customary in the separation art, a portion of the liquid effluent may be recycled to the absorber 20. The concentration of EpB in the liquid effluent stream 24 may vary from about 2 weight percent to about 50 weight percent based on the total weight of the stream with an EpB concentration in the range of about 10 weight percent to about 40 weight percent being normal. Desirably, the liquid effluent stream 24 contains at least 95% of the EpB fed to the absorber 20 via the epoxidation feed stream 10. Preferably, the liquid effluent stream 24 contains greater than 99% of the EpB fed to the absorber 20 via the epoxidation feed stream 10, and more preferably greater than about 99.5% of the EpB fed to the absorber 20 via the epoxidation feed stream 10. One skilled in the art will understand that the amount of EpB so absorbed may be based on either weight % or mole %. The liquid effluent 24 may also contain up to about 20 mole percent water, diol and other materials, and preferably less than about 10 mole percent water and less than about 10 mole percent diol. The mole ratio of the butane to butadiene in the liquid effluent is about the same as the butane:butadiene mole ratio of the liquid absorbent fed to the absorber 20.

Figure 2:
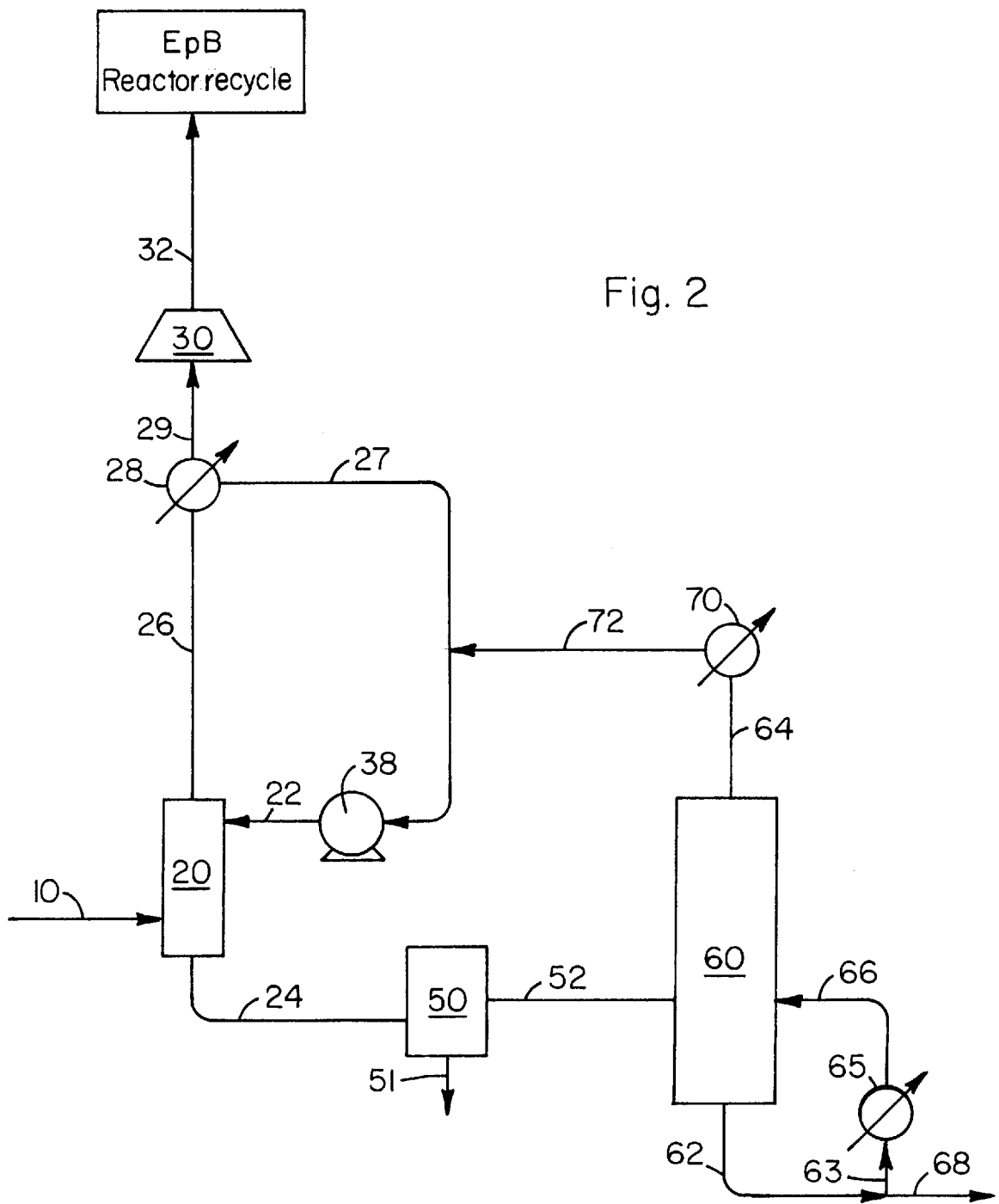
FIG. 2 is a schematic view of another embodiment of the present invention for recovering EpB from an epoxidation reactor effluent wherein a portion of the overhead product is returned to the absorber.

FIG. 2 schematically illustrates another embodiment of the present invention for the recovery of EpB from a substantially vaporous epoxidation effluent. The process is similar to that described above for FIG. 1 and includes the steps of contacting the epoxidation reactor effluent 10 with an effective amount of absorbent, via line 22, to absorb essentially all of the EpB present in the reactor effluent to produce an EpB-rich first liquid effluent, via line 24 and an EpB-lean first vaporous effluent, via line 26 from the absorber. The first vaporous effluent is fed to a condenser 28 where at least a portion of the first vaporous effluent is condensed to form a second liquid effluent. Suitable coolants for condensing at least a portion of the first vapor effluent typically have a boiling point of from about –25° C. to about 5° C. and include such well know materials as chlorofluorocarbons, hydrocarbons, water, hydrofluorocarbons, perfluorocarbons, chilled brine and chilled glycol.

The second liquid effluent is separated from the vaporous material using techniques known to those skilled in the art and at least a portion of the second liquid effluent is fed, via line 27, to a pump 38. The pump 38 increases the pressure of the second liquid effluent to about 5 to about 12 bar and preferably from about 5 to about 7.5 bar. The pressurized second liquid effluent is then returned to the absorber 20 via the absorbent feed line 22 or using a separate line to the absorber 20 (not shown). Desirably, from about 25% to 100% of the second liquid effluent is recycled back to the absorber 20. As discussed above, the significant pressure differential between the returned second liquid effluent/absorbent and the absorber 20 causes flash vaporization of at least a portion of the second liquid effluent/absorbent feed in or proximate to the absorber 20 to produce a temperature of less than about 40° C. and a pressure of less than about 4 bar in the absorber.

The off-gases from the condenser 28 are fed via line 29 to a compressor 30. The compressor can be a single stage or multi-stage compressor designed to increase the pressure of the condenser off-gases to a pressure of less than about 15 bar, with pressures less than about 10 bar being preferred and pressures from about 2 bar to about 10 bar being more preferred. The compressed effluent from the compressor 30 is recycled back to the epoxidation reaction system.

The first liquid effluent stream from the base of the absorber 20 and is fed to a butane/butadiene recovery zone via line 24. The first liquid effluent includes a solution of EpB in butane and butadiene. The concentration of EpB in the first liquid effluent stream may vary from about 10 to about 40 weight percent based on the total weight of the? constituents in the stream. Normally, the EpB concentration is from about 5 to 30 weight percent. The mole ratio of the butane to butadiene in the first liquid effluent is about the same as the butane:butadiene mole ratio of the liquid solvent feed to the absorber 20.

The first liquid effluent may also include up to about 20 mole percent of water, diol and other materials that may be separated from first liquid effluent using methods well known in the art, such as a separation tank 50 and a decanting line 51, prior to being fed to the butane/butadiene recovery zone via line 52.

The butane/butadiene recovery zone includes a distillation column 60, a heat source 65 at the base of the distillation column 60, and a cooling means 70 for condensing vapor removed from the top of the distillation column 60. The first liquid effluent may be fed to the mid-section of the distillation column 60 via line 52. The conditions employed within the butane/butadiene distillation column 60 can vary depending on the particular apparatus employed. The operating temperature of the distillation column 60 is normally within the range of about 5° C. to about 150° C., and preferably from about 100° C. to about 130° C. The operating pressure of the distillation column 60 is normally within the range of about 2 to about 8 bars, and preferably from about 2 to about 6 bars with the pressure and temperature at the top of the column ranging from about 4 to about 5 bar and about 40° C. to about 50° C. The operating pressure of the distillation column 60 may be less than the pressure of the recycle line 72 to the absorber 20 provided a means (not shown) for increasing the pressure of the recycled butane and butadiene mixture recovered is included.

To prevent the formation of butadiene polymerization products, recovery of the butane/butadiene preferably is carried out in the presence of a polymerization inhibitor known to those skilled in the art. For example, suitable polymerization inhibitors include tertiary butyl catechol or an aromatic amine oxide compound, such as Actrene 230 supplied by Exxon. The polymerization inhibitor may be added to the upper section of the butane/butadiene distillation column 60. The formation of low molecular weight, butadiene polymerization products are substantially suppressed by the addition of about 300 to 400 ppm Actrene 230 inhibitor, based on the amount of vapor removed from the column. The inhibitor addition point can be any place that is convenient for the operation of the distillation column 60 by means of a low-flow addition device such as a syringe pump.

A vapor effluent comprising butane and butadiene is removed from the distillation column 60 via line 64, condensed in heat exchanger 70 using a suitable cooling media, such as water, chilled brine or glycol, and recycled back to the absorber 20 by line 72. The pressure of the recycled butane/butadiene mixture in line 72 should be sufficient to allow the mixture to be recycled back to the absorber 20, and desirably, is from about 8 bar to about 12 bar.

Crude EpB is removed from the bottom of the distillation column 60 via line 62. The crude EpB stream may be further refined by one or more distillation processes to increase the purity of the EpB up to 99% or more.

The heat required to vaporize butane and butadiene in the distillation column 60 is provided by recycling via line 62 a portion of the distillation column bottoms liquid stream to a reboiler 65 and then back to the distillation column 60.

Advantageously, fresh butadiene may be added at any point in the recycle loop and it is not necessary that the makeup butadiene be added in the liquid mixture of butane and butadiene fed to the absorber 20.

Figure 3:
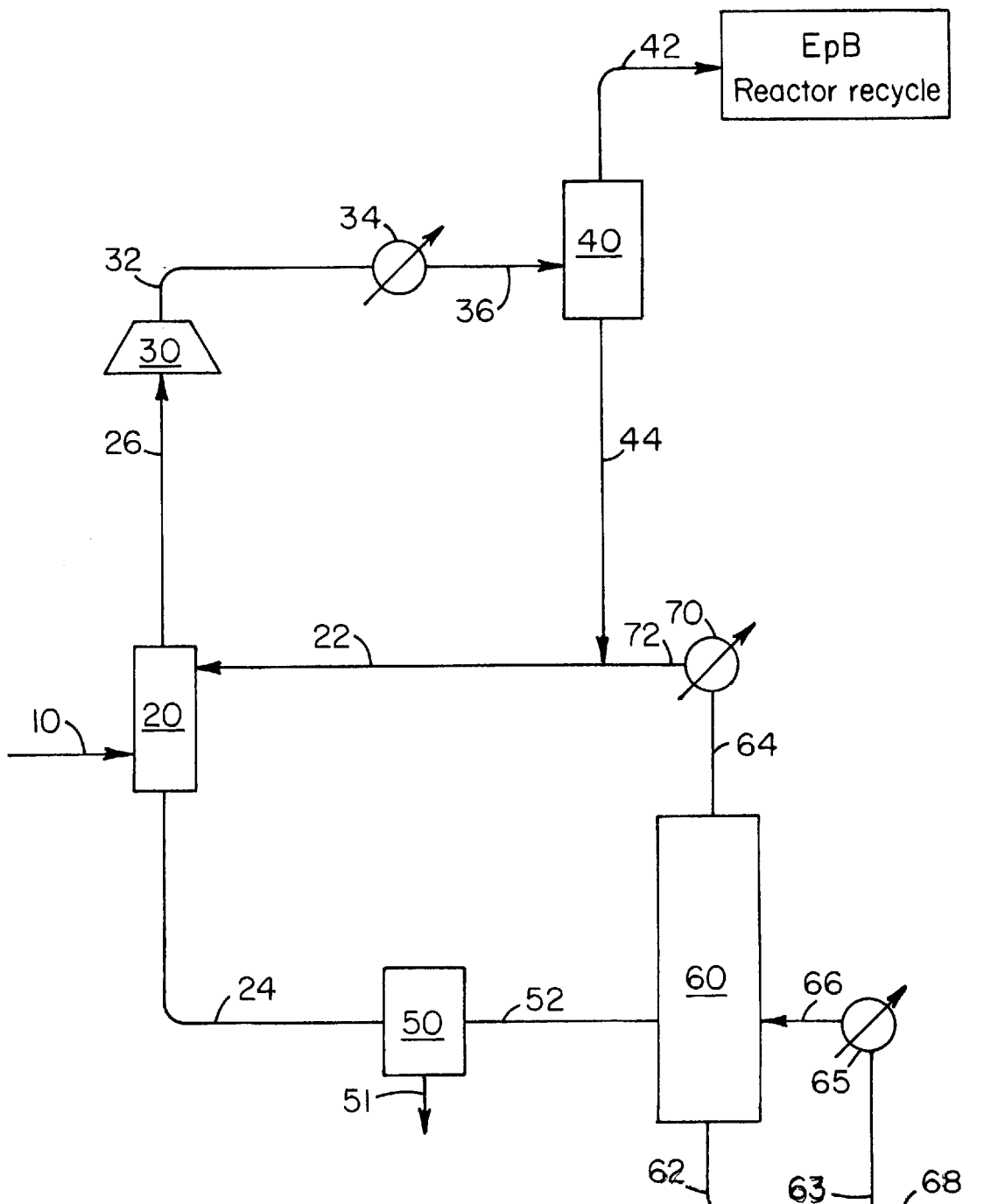
FIG. 3 is a schematic view of another embodiment of the present invention wherein a portion of the overhead product is returned to the absorber.

Referring to FIG. 3, another embodiment of the present invention for recovering EpB from the effluent of an epoxidation reactor is illustrated. The process is similar to that described in FIG. 2 except the first vaporous effluent from the absorber 20 is fed, via line 26, to compressor 30. In a preferred embodiment, the compressed stream is fed, via line 32, to heat exchanger 34 where the temperature of the compressed absorbent is reduced to about 20° C. to about 70° C., and preferably to about 25° C. to about 50° C. Alternatively, if the temperature of stream 32 is low and the pressure increase achieved in compressor 30 is relatively small, heat exchanger 34 may be by-passed.

The compressed stream is fed via line 36 to a vapor-liquid separator 40 where a second vapor stream and is separated from the second liquid stream via lines 42 and 44, respectively. The vapor-liquid separator 40 is typically operated at a pressure at or substantially the same as that of the compressor discharge pressure, i.e., preferably less than about 15 bar and preferably less than about 10 bar. A portion of the second liquid stream via line 44 is returned to the absorber 20 via line 22 or a separate line, not shown.

Figure 4:
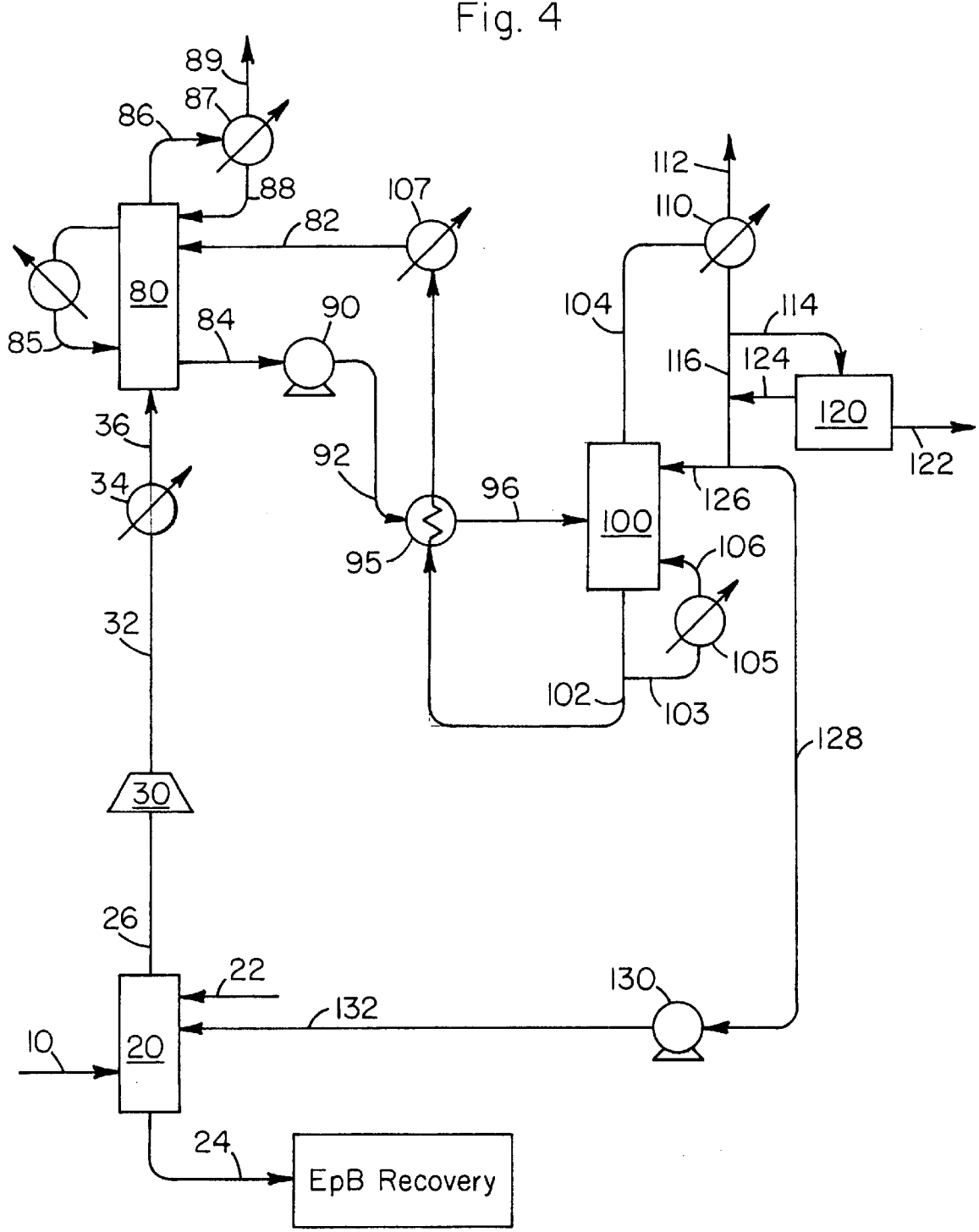
FIG. 4 is a schematic view of another embodiment of the present invention illustrating a recovery process for recovering vaporous EpB from an epoxidation reactor effluent.

FIG. 4 illustrates another embodiment of the invention for recovering EpB from the effluent of an epoxidation reactor. This embodiment is similar to that described above for FIG. 1 and includes contacting the epoxidation reactor effluent with an effective amount of a liquid absorbent to produce a first vaporous effluent lean in EpB and a first liquid effluent rich in EpB. This embodiment further includes contacting the first vaporous effluent with a second absorbent to produce a first-absorbent lean second vaporous effluent and a first-absorbent rich second liquid effluent, recovering at least a portion of the first absorbent from the second liquid effluent to produce a third liquid effluent, returning at least a portion of the third liquid effluent to the absorber at a pressure greater than the pressure of the absorber, and vaporizing at least a portion of the returned third liquid effluent in or near the absorber to produce a temperature of less than about 40° C. and a pressure of less than about 4 bar in the absorber. Referring to FIG. 4 in greater detail, a substantially non-reactive coolant enters the absorber 20, via line(s) 22 and/or 132, at a pressure substantially greater than the operating pressure of the absorber 20 so that as the coolant enters the absorber 20 it vaporizes, causing cooling by direct contact with the absorbent, absorber 20, and/or reactor effluent stream. Alternatively, the coolant and absorbent can be intermixed and introduced into the absorber 20 in the same line 22, in which case the feed line will contain both absorbent and coolant constituents. Desirably, the absorber 20 and its contents are cooled to a temperature of less than about 40° C. Preferably, the absorber 20 and its contents are cooled to a temperature of from about 0° C. to about 25° C. and are at a pressure of about 1.0 to about 3.5 bar, and more preferably, the absorber 20 and its contents are cooled to a temperature from about 2° C. to about 15° C. and are at a pressure of about 1.0 to about 3 bar and most preferably are at a pressure of from about 1 to about 2 bar.

An effective amount of a non-reactive first absorbent is introduced into the absorber 20 via line 22 and counter-currently contacts the epoxidation reactor effluent 10 to produce an EpB rich liquid stream 24 and an absorbent/coolant, hereinafter collectively referred to as "first absorbent", rich vapor stream 26 that is essentially free of EpB. Desirably, the first absorbent rich vapor stream 26 is pressurized in compressor 30 to a pressure of less than about 15 bar, preferably to a pressure of less than about 10 bar and more preferably to a pressure ranging from about 2.75 to about 7.5 bar, and optionally, fed via line 32 to heat exchanger 34 where the temperature is reduced to about 20° C. to about 70° C., and preferably to about 25° C. to about 50° C. using cooling water. Alternatively, if the temperature of stream 32 is low and the pressure increase achieved in compressor 30 is relatively small, heat exchanger 34 may be by-passed or omitted.

Gas stream 36 is fed to the bottom of a second absorber 80, contacted with a second absorbent, fed to the second absorber 80 via line 82, where the first absorbent component is at least partially recovered from the gas stream 36 to produce a first-absorbent lean second vaporous effluent, via line 86 and a first-absorbent rich second liquid effluent, via line 84. The second absorbent flows counter-currently to the first absorbent rich vapor stream. The temperature within the second absorber 80 is from about 15° C. to about 80° C., more preferably from about 25° C. to about 40° C. The second absorber 80 contains a suitable packing material or trays as described above to provide intimate vapor-liquid contact. Depending on the selected second absorbent and absorbent flow rate, the second absorber 80 can have an equivalent of about 1 to 15 theoretical equilibrium stages, preferably 2 to 10 theoretical equilibrium stages. The molar ratio of the second absorbent, fed via line 82, to the first absorbent, fed to the second absorber via line 36, is typically from about 0.5:1 moles per mole to about 8:1 moles per mole, and preferably from about 1:1 to about 4:1 moles per mole.

Absorbents suitable for use in the second absorber 80 include $C_4$ to $C_{20}$ hydrocarbons, $C_4$ to $C_{20}$ alkanols, $C_6$ to $C_{22}$ carboxylic acid esters, $C_2$ to $C_4$ carbonates, chlorofluorocarbons, hydrofluorocarbons, perfluorocarbons and mixtures thereof. Compounds from the aforementioned list with normal boiling points above 100° C. are advantageous and, more desirably above 115° C. to limit losses of absorbent to the absorber off-gas. Preferably, both the first and second absorbents are selected from the group consisting of n-butane, isobutane, isopentane and mixtures thereof.

Although the first and second absorbers 20 and 80 are illustrated as two separate pieces of equipment, it is contemplated to be within the scope of the present invention, and one skilled in the art will understand, that the absorption zones 20 and 80 may be combined within a single column shell if desired with the upper section of the absorber separated from the lower section by any appropriate partitioning device known in the art such as a chimney tray with a total liquid draw-off sump.

Generally, the heat of absorption for the first absorbent is large and causes a substantial temperature rise across the second absorber 80. To improve recovery efficiency and lower the ratio of second absorbent, line 82, to first absorbent, line 36, the second absorber 80 may be provided with one or more interstage coolers, such as heat exchanger 85 at various places in the column. Liquid is withdrawn from a tray or sump and diverted through heat exchanger 85, where the heat of absorption is removed using methods that are conventional in the art such as by heat transfer against a suitable cooling media, e.g., water, glycol, or chilled brine. The cooled liquid is then returned to the second absorber 80 at a point in the column lower than the withdrawal point, typically just one or two stages below the withdrawal point. When advantageous, one or more intercoolers may be placed in the lower section of the column, typically 1 to 4 stages from the bottom. Additional cooling may also be provided by using an overhead partial condenser 87. The first-absorbent lean vaporous second effluent from the second absorber 80 is conveyed via line 86 to partial condenser 87, cooled and the condensed liquids returned to the second absorber 80 via line 88. Non-condensable gases such as oxygen, carbon dioxide, and insubstantial amounts of epoxidation reaction diluent gas, such as, n-butane, butadiene, and small amounts of the first and second absorbents exit via line 89 which may be further processed to recover the n-butane and butadiene using techniques known to those skilled in the art. Depending on the volatility of the second absorbent 82 used for absorbing the first absorbent 36, the partial condenser 87 may serve to substantially reduce the quantity of the absorbents leaving the absorber 80 and reduce the amount of make-up first and second absorbents needed. Desirably, less than about 0.1 weight %, preferably less than about 0.01 weight % and more preferably less than 0.001 weight % of the first absorbent exits via line 89. If the second absorbent 82 is substantially non-volatile under conditions at which second absorber 80 is operated, the partial condenser 87 may be eliminated or by-passed. The second absorber 80 overhead may then be further processed to remove carbon dioxide before recycling to an epoxidation reactor. Suitable carbon dioxide removal systems are known to those skilled in the art. Examples of such carbon dioxide scrubbing systems include contacting the carbon dioxide containing stream with an alkali metal hydroxide in another absorption process or alternatively using a hot carbonate carbon dioxide removal system well known to those skilled in the art.

The second liquid effluent exits the bottom of the absorber 80 via line 84. The pressure of the second liquid effluent in line 84 is increased for recovery of the first and second absorbents to a pressure of about 3to about 15 bar by the action of pump 90. The pressurized second effluent stream is conveyed via line 92 to an optional interchanger 65, where stream 92 is heated by exchange with hot distillation bottoms product 102 before introduction, via line 96, into the distillation column 100. The use of a heat interchanger is advantageous since it substantially reduces the overall energy consumption of the process.

Distillation column 100 separates the first absorbent from the second absorbent. The section of the distillation column 100 above the feed stream 96 serves to reduce the concentration of the first absorbent in the overhead vapor stream 104 to very low levels, desirably, less than 1000 part per million by weight (ppmw), and more desirably less than 500 ppmw. This portion of the distillation column 100 typically contains from 2 to 10 theoretical equilibrium stages and more typically 2 to 6 theoretical equilibrium stages. The stripping zone of the distillation column 100, that is the section of distillation column 100 below the feed stream 96, typically contains 2 to 10 theoretical equilibrium stages, and more typically 2 to 6 theoretical equilibrium stages. The third liquid effluent bottoms stream 102 is split and reboiler stream 103 is fed to a reboiler 105. Heat to the reboiler 105 may be supplied by any suitable heating media, although steam of appropriate pressure is preferred. Steam may be provided to the bottom of the distillation column 100 to assist in the stripping of the refrigerant from the solvent. Advantageously, the use of steam tends to lower the heat duty in reboiler 105, reducing thermal reactions of residual butadiene. Steam addition rates are preferably 0.25:1 to 20:1 moles steam per mole of refrigerant, more preferably 1:1 to 7:1 moles per mole.

The overhead vapor stream 104 is condensed to form a third liquid effluent using heat exchanger 110 with a suitable cooling media, such as water. The non-condensable constituents exit via line 112. If capable of forming two phases, the condensed vapors may be conveyed via line 114 to a decanting vessel 120 for separation into two liquid layers. The bottom aqueous phase from the decanting vessel 120 is removed via line 112 and may further be treated for removal of trace organic compounds using steam stripping. Organic materials are removed from the decanting vessel 120 via line 124 which may be split into a reflux stream 126 and a product distillate stream 128. The molar reflux ratio is typically from about 0.2 to about 10.0, and preferably from about 0.4 to about 5.0. The operating pressure for the distillation column 100 is dictated by the temperature required to condense the first absorbent vapor in stream 104. Typical pressures for the distillation column 100 are from about 3 to about 15 bar, and preferably from about 5 bar to about 7 bar, in order to keep the bottoms temperature below about 230° C. At least a portion of the third liquid effluent is fed via line 28 to pump 130 where the pressure of the third liquid effluent is increased to about 5 to about 12 bar and desirably from about 5 to about 7.5 bar. The pressurized third liquid effluent is returned to the absorber 20 via line 132 or it may be fed to the absorber via fee line 22.

Optionally, steam may be provided to the bottom section of the distillation column 100 to assist in stripping the first absorbent from the second absorbent. Moreover, the addition of steam tends to lower the heat duty on the reboiler 105 and reducing thermal reactions of residual butadiene. Steam addition rates are preferably from about 0.25:1 to about 20:1 moles of steam per mole of first absorbent, and more preferably from about 1:1 to about 7:1 of steam per mole of first absorbent.

The distillation column tails or bottoms 102 is optionally cooled using the interchanger 95 as described above. The bottoms 102 may be further cooled using heat exchanger 107 before being recycled to the second absorber 80 via line 82. Stream 82 is cooled to less than about 120° C., and preferably less than about 40° C. Make-up second absorbent may be added at any location convenient for process operations to maintain the circulation rate within the absorbent recycle loop. Desirably, absorbent losses of both the first and second absorbents are less than about 0.02 kilograms per kilogram of EpB produced, and preferably are less than about 0.01 kg per kg of EpB produced.

If desired, to prevent the formation of butadiene polymerization products, a butadiene polymerization inhibitor, such as a phenolic compound such as tertiary butyl catechol or an amine oxide such as Actrene 230 supplied by Exxon Corporation or other like inhibitors known in the art, may be added to the second absorbent-regeneration loop to reduce losses of butadiene to thermal reactions.

Figure 5:
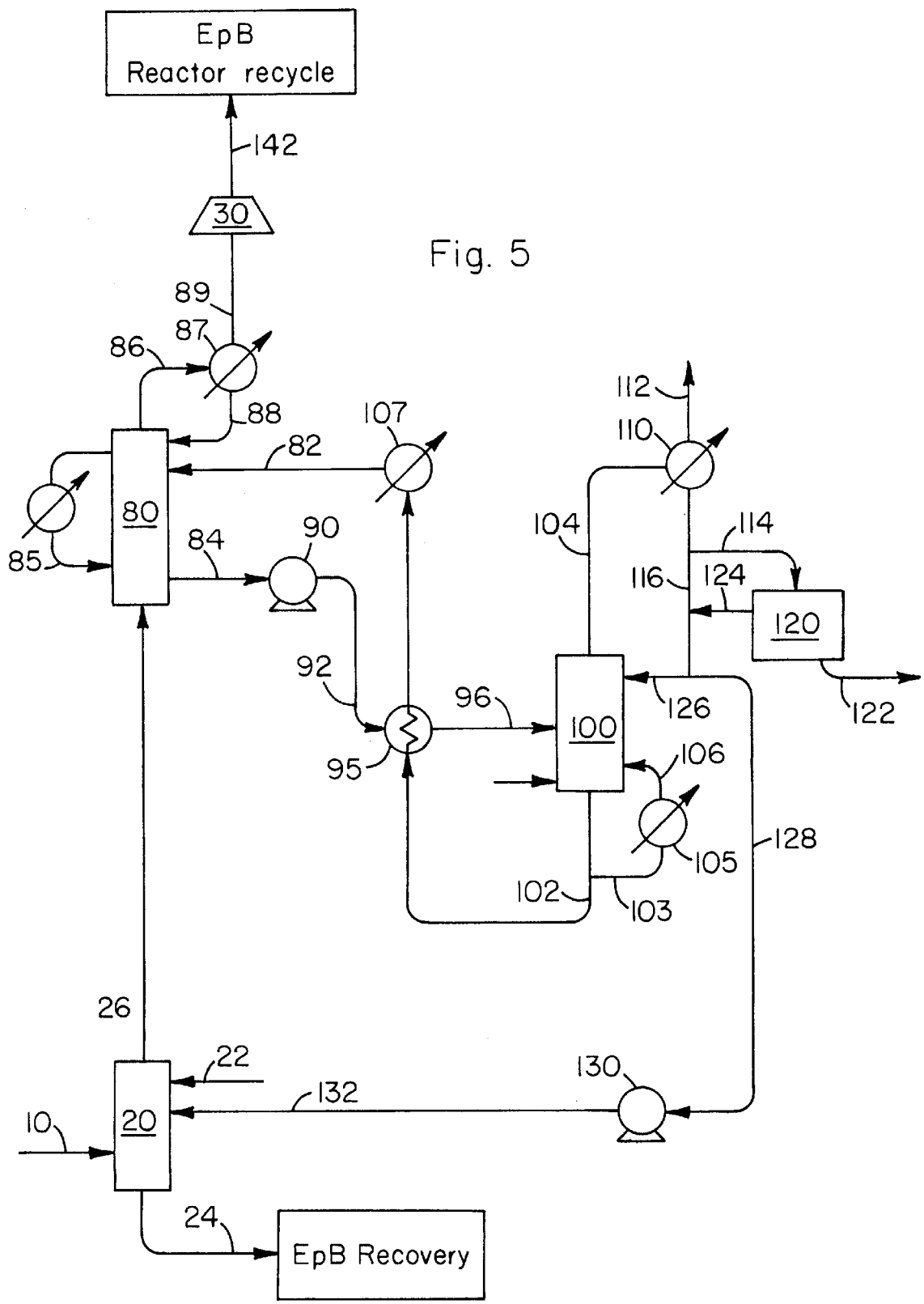
FIG. 5 is a schematic view of another embodiment of the present invention illustrating a recovery process for recovering vaporous EpB from an epoxidation reactor effluent.

Referring to FIG. 5, another embodiment for recovering EpB from the effluent of an epoxidation reactor in accordance with the present invention is illustrated. This embodiment is similar to that described above for FIG. 4 except the first vaporous effluent exiting the absorber 20 via line 26 is not compressed prior to being contacted in the second absorber 80 with the second absorbent added via line 82. Accordingly, the second absorber 80 is operated at a much lower pressure than that described above for FIG. 4, typically from about 1 to about 3 bar. Additionally, the second vaporous effluent removed via line 86 is compressed to a pressure of less than about 15 bar using compressor 30 prior to recycling to the epoxidation reactor.

Although not illustrated in FIGS. 4 and 5, one skilled in the art will understand that these embodiments may further include a butane/butadiene recovery zone similar to that described above for FIG. 2 where EpB in stream 24 is recovered. Moreover, at least a portion of the butane and butadiene recovered in such recovery zone may be recycled back to the absorber 20 using a separate feed line (not shown) or can be fed to the absorber 20 in conjunction with the first absorbent feed via line 22 or the recycled third liquid effluent via line 132.

The present invention is illustrated in greater detail by the specific examples presented below. It is to be understood that these examples are illustrative embodiments and are not intended to be limiting of the invention, but rather are to be construed broadly within the scope and content of the appended claims.

EXAMPLE 1

This example illustrates the effect of the absorber temperature on the pressure required in the first absorption zone and the maximum safe oxygen concentration when using a 4:1 molar mixture of n-butane and butadiene as the absorbent in the first absorber. The results are in Table 1 below.

TABLE 1

| Temperature (° C.) | Absorber Pressure (bar) | Maximum Safe Oxygen (%) |
|---|---|---|
| −4 | 1.42 | 42.6 |
| 0 | 1.48 | 42.1 |
| 12 | 2.37 | 34.4 |
| 24 | 3.35 | 33.0 |
| 30 | 4.31 | 30.3 |
| 40 | 5.63 | 27.4 |
| 60 | 9.45 | 21.8 |
| 80 | 18.68 | 14.5 |

In accordance with the invention, at temperatures below 25° C. the operational pressure of the absorber is less than 4 bar. It can further be seen from Table 1 that at temperatures above 25° C. the operational pressure of the absorber is in excess of 4 bar which contra to the invention.

For examples 2–4, computer simulations were run using an IBM RS6000 computer running the ASPEN PLUS* version 9 process simulator software.

EXAMPLE 2

The following computer simulation illustrates the efficacy of the present invention in recovering EpB and other materials used in its recovery. All stream numbers given in Table 2 refers to designations as depicted in FIG. 4. Both the absorbent and the coolant profiled in the absorber are n-butane. Absorber 20 consists of ten theoretical equilibrium stages. Butane absorbent stream 22 is fed to the top stage and the coolant 132 is fed to the middle section of absorber 20. The second absorber 80 consists of two theoretical equilibrium stages with a partial condenser on the gas outlet stream 86. The absorbent recovery zone includes a distillation column 100 consisting of five theoretical equilibrium stages. The molar reflux ratio is 0.59. Theoretical material balances, temperatures, and pressures of selected process streams from the computer modeling are given in Table 2. Temperatures are given in degrees centigrade, pressures are in bar, and component flow rates are in kg/hr. The maximum safe oxygen content of the recycle loop, as dictated by the compressor outlet pressure and temperature is 29 mole percent.

TABLE 2

| Stream No | Temp. (° C.) | Press. (bar) | $O_2$ | $CO_2$ | Water | Butadiene | n-Butane | EpB | n-Decane |
|---|---|---|---|---|---|---|---|---|---|
| 10 | 45 | 1.59 | 498.9 | 88.0 | 67.0 | 371.6 | 3483.3 | 208.2 | 0 |
| 22 | 45 | 6.62 | 0 | 0 | 0 | 324.5 | 1046.2 | 3.5 | 0 |
| 132 | 48 | 5.66 | 0 | 0 | 1.9 | 394.7 | 1865.9 | 1.9 | 0 |
| 24 | 5 | 1.59 | 1.0 | 2.0 | 60.7 | 91.6 | 1047.8 | 211.0 | 0 |
| 26 | 2 | 1.52 | 497.9 | 86.0 | 7.5 | 999.3 | 5347.7 | 2.6 | 0 |
| 32 | 43 | 3.79 | 497.9 | 86.0 | 7.5 | 999.3 | 5347.7 | 2.6 | 0 |
| 82 | 45 | 3.79 | 0 | 0 | 0 | 9.3 | 136.1 | >0.1 | 3585.2 |
| 84 | 47 | 3.72 | 2.5 | 2.0 | 1.2 | 404.0 | 2002.2 | 1.9 | 3571.3 |

TABLE 2-continued

| Stream | Temp. | Press. | Component Flow rates (kg/hr) | | | | | | |
|---|---|---|---|---|---|---|---|---|---|
| No | (° C.) | (bar) | $O_2$ | $CO_2$ | Water | Butadiene | n-Butane | EpB | n-Decane |
| 89 | 45 | 3.79 | 495.3 | 84.0 | 6.3 | 604.5 | 3481.6 | 0.7 | 13.9 |
| 96 | 137 | 5.00 | 2.5 | 2.0 | 1.2 | 404.0 | 2002.2 | 1.9 | 3571.3 |
| 112 | 47 | 4.97 | 2.5 | 2.0 | 0 | 0 | 0 | 0 | 0 |
| 128 | 48 | 4.97 | 0 | 0 | 1.2 | 394.8 | 1866.1 | 1.9 | 14.3 |
| 102 | 230 | 5.00 | 0 | 0 | 0 | 9.3 | 136.0 | >0.1 | 3556.8 |

EXAMPLE 3

The following computer simulation illustrates the efficacy of the present invention in recovering EpB and other materials used in its recovery. All stream numbers given in Table 3 refers to designations as depicted in FIG. 5. Both the absorbent and the coolant profiled in the absorber are n-butane. Absorber 20 consists of ten theoretical equilibrium stages. Butane absorbent stream 22 is fed to the top stage and the coolant 132 is fed to the middle section of absorber 20. The second absorber 80 consists of five theoretical equilibrium stages with a partial condenser on the gas outlet stream 86. Distillation column 100 consists of eight theoretical equilibrium stages. The molar reflux ratio is 0.58. Theoretical material balances, temperatures, and pressures of selected process streams are given in Table 3. Temperatures are given in degrees centigrade, pressures are in bar, and component flow rates are in kg/hr. The maximum safe oxygen content of the recycle loop, as dedicated by the compressor outlet pressure and temperature is 29 mole percent.

EXAMPLE 4

The following computer simulation illustrates the efficacy of the present invention in recovering EpB and other materials used in its recovery using n-butanol instead of n-decane. All stream numbers given in Table 4 refers to designations as depicted in FIG. 5. Both the absorbent and the coolant profiled in the absorber are n-butane. Absorber 20 consists of ten theoretical equilibrium stages. Butane absorbent stream 22 is fed to the top stage and the coolant 132 is fed to the middle section of absorber 20. The second absorber 80 consists of five theoretical equilibrium stages with a partial condenser on the gas outlet stream 86. Distillation column 100 consists of twelve theoretical equilibrium stages. The molar flux ratio is 0.80. Theoretical material balances, temperatures, and pressures of selected process streams are given in Table 4. Temperatures are given in degrees centigrade, pressures are in bar, and component flow rates are in kg/hr. The maximum safe oxygen content of the recycle loop, as dictated by the compressor outlet pressure and temperature is 29 mole percent.

TABLE 3

| Stream | Temp. | Press. | Component Flow rates (kg/hr) | | | | | | |
|---|---|---|---|---|---|---|---|---|---|
| No | (° C.) | (bar) | $O_2$ | $CO_2$ | Water | Butadiene | n-Butane | EpB | n-Decane |
| 10 | 45 | 1.59 | 498.9 | 88.0 | 67.0 | 371.6 | 3483.3 | 208.2 | 0 |
| 22 | 45 | 6.62 | 0 | 0 | 0 | 324.5 | 1046.2 | 3.5 | 0 |
| 132 | 48 | 5.86 | 0 | 0 | 1.9 | 415.0 | 1825.5 | 2.1 | 0.7 |
| 24 | 5 | 1.59 | 1.0 | 1.9 | 60.9 | 88.3 | 1047.9 | 211.3 | 0.7 |
| 26 | 2 | 1.52 | 497.9 | 86.1 | 8.1 | 1022.8 | 5307.2 | 2.5 | 0 |
| 82 | 45 | 1.66 | 0 | 0 | >0.1 | 33.0 | 552.7 | 0.1 | 14261.1 |
| 84 | 38 | 1.52 | 2.2 | 2.0 | 1.9 | 448.0 | 2378.2 | 2.2 | 14200.0 |
| 86 | 45 | 1.45 | 495.6 | 84.1 | 6.2 | 607.9 | 3481.6 | 0.4 | 61.1 |
| 142 | 91 | 3.72 | 495.7 | 84.1 | 6.2 | 607.9 | 3481.6 | 0.4 | 61.1 |
| 92 | 129 | 5.00 | 2.2 | 2.0 | 1.9 | 448.0 | 2378.2 | 2.2 | 14200.0 |
| 112 | 39 | 6.14 | 2.2 | 2.0 | 0 | 0 | 0 | 0 | 0 |
| 128 | 47 | 4.96 | 0 | 0 | 1.9 | 448.0 | 1825.6 | 2.1 | 0.7 |
| 102 | 230 | 5.00 | 0 | 0 | >0.1 | 33.0 | 552.7 | 0.1 | 14199 |

TABLE 4

| Stream | Temp. | Press. | Component Flow rates (kg/hr) | | | | | | |
|---|---|---|---|---|---|---|---|---|---|
| No | (° C.) | (bar) | $O_2$ | $CO_2$ | Water | Butadiene | n-Butane | EpB | n-Decane |
| 10 | 45 | 1.59 | 498.9 | 88.0 | 67.0 | 371.6 | 3483.3 | 208.2 | 0 |
| 22 | 45 | 6.62 | 0 | 0 | 0 | 324.5 | 1046.2 | 3.5 | 0 |
| 132 | 47 | 5.66 | 0 | 0 | 8.4 | 457.8 | 2121.0 | 1.8 | 7.4 |
| 24 | 5 | 1.59 | 0.9 | 2.1 | 65.6 | 92.5 | 1046.7 | 210.9 | 200.8 |
| 26 | 2 | 1.52 | 497.9 | 85.9 | 9.8 | 1061.5 | 5450.4 | 2.5 | 0.1 |

TABLE 4-continued

| Stream No | Temp. (° C.) | Press. (bar) | $O_2$ | $CO_2$ | Water | Butadiene | n-Butane | EpB | n-Decane |
|---|---|---|---|---|---|---|---|---|---|
| 82 | 45 | 1.66 | 0 | 0 | 11.0 | 25.5 | 128.4 | 7.6 | 29909. |
| 84 | 40 | 1.52 | 0.1 | 0.3 | 19.3 | 483.3 | 2249.3 | 9.4 | 29715. |
| 86 | 45 | 1.45 | 497.9 | 85.6 | 1.4 | 603.7 | 3329.5 | 0.8 | 194.0 |
| 142 | 91 | 3.72 | 497.9 | 85.6 | 1.4 | 603.6 | 3329.5 | 194.0 | 0.8 |
| 92 | 52 | 6.62 | 0.1 | 0.3 | 19.3 | 483.3 | 2249.3 | 9.3 | 29715. |
| 112 | 40 | 6.14 | 0.1 | 0.3 | 0 | 0 | 0 | 0 | 0 |
| 128 | 47 | 4.96 | 0 | 0 | 8.4 | 457.8 | 2121.0 | 1.8 | 7.4 |
| 102 | 170 | 5.00 | 0 | 0 | 11.0 | 25.5 | 128.4 | 7.6 | 28709. |

Although the present invention has been described in terms of the presently preferred embodiments, it is to be understood that such disclosure is not to be interpreted as limiting to the invention described herein. No doubt that after reading the disclosure, various alterations and modifications will become apparent to those skilled in the art to which the invention pertains. It is intended that the appended claims be interpreted as covering all such alterations and modifications as fall within the spirit and scope of the invention.

We claim:

1. A process for recovering EpB from a vapor phase epoxidation reactor effluent comprising:
   a. contacting said epoxidation reactor effluent with an effective amount of a liquid absorbent in an absorber to absorb essentially all of the EpB present in the epoxidation reactor effluent; and
   b. vaporizing proximate to the absorber an effective amount of a non-reactive coolant to cool the absorber to a temperature of less than about 40° C. and a pressure of less than about 4 bar.

2. The process of claim 1 wherein said absorbent is selected from the group consisting of $C_3$ to $C_{20}$ hydrocarbons which do not form azeotropes with EpB, $C_4$ to $C_{20}$ alkanols, $C_6$ to $C_{22}$ carboxylic acid esters, $C_2$ to $C_4$ carbonates and mixtures thereof.

3. The process of claim 2 wherein said absorbent is selected from the group consisting of n-butane, isobutane, isopentane, 1,3-butadiene and mixtures thereof.

4. The process of claim 3 wherein said mixture of n-butane and 1,3-butadiene has a mole ratio of from about 20:1 to about 1:2.

5. The process of claim 1 wherein said coolant is selected from the group consisting of $C_3$ to $C_5$ hydrocarbons, chlorofluorocarbons, hydrofluorocarbons, perfluorocarbons and mixtures thereof having normal boiling points between −42° C. and 15° C.

6. The process of claim 5 wherein said coolant is selected from the group consisting of n-butane, isobutane, isopentane and mixtures thereof.

7. The process of claim 6 wherein said absorber is cooled to a temperature of about 0° C. to about 40° C. and operates at a pressure of about 1.0 to about 3.5 bar.

8. The process of claim 1 where in said absorber is cooled to a temperature of about 2° C. to about 15° C. and is operated at a pressure of about 1.0 to about 3.0 bar.

9. The process of claim 1 wherein said absorber has less than about 15 theoretical equilibrium stages and a liquid effluent from said absorber contains greater than about 95% of the amount of EpB fed to said absorber from said epoxidation reactor effluent.

10. The process of claim 9 wherein said liquid effluent from said absorber contains greater than about 99% of the EpB fed to said absorber from said epoxidation reactor effluent.

11. The process of claim 9 wherein said liquid effluent from said absorber contains greater than about 99.5% of the EpB fed to said absorber from said epoxidation reactor effluent.

12. The process of claim 1 further comprising compressing a vaporous effluent from said absorber, condensing at least a portion of said vaporous effluent to form a second liquid effluent and returning at least a portion of said liquid effluent to said absorber at a pressure greater than about 4 bar.

13. A process for recovering EpB from a vapor phase epoxidation reactor effluent having EpB, butane and butadiene constituents, said process comprising:
   a. contacting said epoxidation reactor effluent with an effective amount of a liquid absorbent in an absorber to produce an EpB lean first vaporous effluent and an EpB rich first liquid effluent;
   b. condensing a portion of said first vaporous effluent to form a second liquid effluent and a second vapor effluent;
   c. returning a portion said second liquid effluent to said absorber at a pressure greater than said absorber; and
   d. vaporizing a portion of said returned second liquid effluent proximate to said absorber to produce a temperature of less than about 40° C. and a pressure of less than about 4 bar in said absorber.

14. The process of claim 13 wherein said absorbent is selected from the group consisting of $C_3$ to $C_{20}$ hydrocarbons which do not form azeotropes with EpB, $C_4$ to $C_{20}$ alkanols, $C_6$ to $C_{22}$ carboxylic acid esters, $C_2$ to $C_4$ carbonates, chlorofluorocarbons, hydrofluorocarbons, perfluorocarbons, and mixtures thereof.

15. The process of claim 14 wherein said absorbent is selected from the group consisting of n-butane, isobutane, isopentane, 1,3-butadiene and mixtures thereof.

16. The process of claim 14 wherein the ratio of absorbent feed to reactor effluent feed fed to the absorber is from about 1:10 to about 1:1, based on weight.

17. The process of claim 13 wherein said absorbent is a mixture of n-butane and 1,3-butadiene having a mole ratio of from about 20:1 to about 1:2.

18. The process of claim 13 wherein said first vaporous effluent contains less than about 0.1 weight % EpB.

19. The process of claim 13 wherein from about 25% to 100% of said second liquid effluent is returned to said absorber at pressure of from about 5 bar to about 12 bar.

20. The process of claim 15 further comprising compressing one of said first or second vaporous effluents to a pressure of less than about 15 bar.

21. The process of claim 20 wherein one of said first or second vaporous effluents is compressed to a pressure of less than about 10 bar.

22. The process of claim 13 further comprising feeding said first liquid effluent to a butane/butadiene recovery zone wherein a portion of the butane and butadiene in said first liquid effluent is recovered and recycled back to said absorber.

23. A process for recovering EpB from a vapor phase epoxidation reactor effluent having from about 0.5 to about 10 mole percent EpB, about 4 to 50 mole percent butadiene, and about 25 to 85 mole percent butane gas, said process comprising:
   a. contacting said epoxidation reactor effluent with an effective amount of a first liquid absorbent in a first absorber to produce an EpB lean first vaporous effluent and an EpB rich first liquid effluent;
   b. contacting said first vaporous effluent with a second liquid absorbent in a second absorber to produce a first-absorbent lean second vaporous effluent and a first-absorbent rich second liquid effluent
   c. recovering at least a portion of said first absorbent from said second liquid effluent to produce a third liquid effluent;
   d. returning at least a portion third liquid effluent to said first absorber at a pressure greater than said absorber; and
   e. vaporizing a portion of said returned third liquid effluent proximate to said absorber to produce a temperature of less than about 40° C. and a pressure of less than about 4 bar in said absorber.

24. The process of claim 23 wherein said first absorbent is selected from the group consisting of $C_3$ to $C_{20}$ hydrocarbons which do not form azeotropes with EpB, $C_4$ to $C_{20}$ alkanols, $C_6$ to $C_{22}$ carboxylic acid esters, $C_2$ to $C_4$ carbonates, chlorofluorocarbons, hydrofluorocarbons, perfluorocarbons and mixtures thereof.

25. The process of claim 23 wherein said first absorbent is selected from the group consisting of n-butane, isobutane, isopentane, 1,3-butadiene and mixtures thereof.

26. The process of claim 25 wherein the ratio of absorbent feed to reactor effluent feed fed to the absorber is from about 1:10 to about 1:1, based on weight.

27. The process of claim 25 wherein said absorbent mixture has a butane and 1,3-butadiene mole ratio of from about 20:1 to about 1:2.

28. The process of claim 23 wherein said second liquid absorbent is selected from the group consisting of $C_4$ to $C_{20}$ hydrocarbons, $C_4$ to $C_{20}$ alkanols, $C_6$ to $C_{22}$ carboxylic acid esters, $C_2$ to $C_4$ carbonates and mixtures thereof.

29. The process of claim 23 further comprising compressing at least one of said first or second vapor effluents to a pressure of less than about 10 bar.

30. The process of claim 23 further comprising feeding said first liquid effluent to a butane/butadiene recovery zone wherein a portion of the butane and butadiene in said first liquid effluent is recovered, condensed and recycled back to said absorber.

31. A process for recovering EpB from a vapor phase epoxidation reactor effluent having EpB, butane and butadiene constituents, said process comprising:
   a. contacting said epoxidation reactor effluent with an effective amount of a first liquid absorbent in a first absorber to produce an EpB lean first vaporous effluent and an EpB rich first liquid effluent;
   b. contacting said first vaporous effluent with a second liquid absorbent in a second absorber to produce a first-absorbent lean second vaporous effluent and a first-absorbent rich second liquid effluent;
   c. recovering at least a portion of said first absorbent from said second liquid effluent to produce a third liquid effluent;
   d. returning at least a portion third liquid effluent to said first absorber at a pressure greater than said absorber;
   e. vaporizing a portion of said returned third liquid effluent proximate to said absorber to produce a temperature of less than about 40° C. and a pressure of less than about 4 bar in said absorber; and
   f. compressing at least one of said first or second vaporous effluents to a pressure of less than about 15 bar.

32. The process of claim 31 wherein said first vaporous effluent is compressed to a pressure to a pressure of less than about 10 bar.

33. The process of claim 31 wherein said first and second absorbents are independently selected from the group consisting of $C_3$ to $C_{20}$ hydrocarbons, $C_4$ to $C_{20}$ alkanols, $C_6$ to $C_{22}$ carboxylic acid esters, $C_2$ to $C_4$ carbonates, chlorofluorocarbons, hydrofluorocarbons, perfluorocarbons and mixtures thereof.

34. The process of claim 31 wherein said first and second absorbents are selected from the group consisting of n-butane, isobutane, isopentane and mixtures thereof.

35. The process of claim 31 wherein the pressure of said returned third liquid effluent is from about 5 to about 12 bar.

36. The process of claim 35 wherein from about 25% to 100% of said third liquid effluent is returned to said first absorber.

37. The process of claim 31 further comprising feeding said first liquid effluent to a butane/butadiene recovery zone wherein a portion of the butane and butadiene in said first liquid effluent is recovered, condensed and recycled back to said absorber.

38. The process of claim 31 wherein said first vaporous effluent contains less than about 250 ppm by weight of EpB.

39. The process of claim 31 wherein said absorber is cooled to a temperature of about 0° C. to about 25° C. and operates at a pressure of about 1.0 to about 3.5 bar.

40. The process of claim 31 where in said absorber is cooled to a temperature of about 2° C. to about 15° C. and is operated at a pressure of about 1.5 to about 3.0 bar.

41. The process of claim 31 wherein said third liquid effluent is vaporized substantially within said absorber.

42. A process for recovering EpB from a vapor phase epoxidation reactor effluent having EpB, butane and butadiene constituents, said process comprising:
   a. contacting said epoxidation reactor effluent with an effective amount of a first liquid absorbent selected from the group consisting of n-butane, isobutane, isopentane, 1,3-butadiene and mixtures thereof in a first absorber to produce an EpB lean first vaporous effluent and an EpB rich first liquid effluent;
   b. contacting said first vaporous effluent with a second liquid absorbent selected from the group consisting of n-butane, isobutane, isopentane and mixtures thereof in a second absorber to produce a first-absorbent lean second vaporous effluent and a first-absorbent rich second liquid effluent
   c. recovering at least a portion of said first absorbent from said second liquid effluent to produce a third liquid effluent;
   d. returning at least a portion third liquid effluent to said first absorber at a pressure of from about 5 to 12 bar;
   e. vaporizing a portion of said returned third liquid effluent proximate to said absorber to produce a temperature of less than about 40° C. and a pressure of less than about 4 bar in said absorber; and
   f. compressing at least one of said first or second vaporous effluents to a pressure of less than about 15 bar.

* * * * *